United States Patent [19]

Callaway

[11] Patent Number: 5,025,801
[45] Date of Patent: Jun. 25, 1991

[54] UNIVERSAL INTRAVENOUS ARM SUPPORT

[76] Inventor: James J. Callaway, 1577 Moran Rd., Franklin, Tenn. 37064

[21] Appl. No.: 432,494

[22] Filed: Nov. 7, 1989

[51] Int. Cl.$^5$ .............................................. A61F 5/37
[52] U.S. Cl. ................................. 128/877; 128/89 R; 128/87 R; 604/135
[58] Field of Search ................. 128/DIG. 6, 877, 879, 128/87 R, 87 A; 604/135, 260

[56] References Cited

U.S. PATENT DOCUMENTS

| | | | |
|---|---|---|---|
| 3,590,817 | 7/1971 | Wresh | 128/877 |
| 3,812,851 | 5/1974 | Rodriguez | 128/877 |
| 4,425,913 | 1/1984 | Lewis | 128/DIG. 6 |
| 4,677,971 | 7/1987 | Lindemann | 128/87 R |
| 4,719,906 | 1/1988 | DeProspero | 128/87 A |
| 4,798,199 | 1/1989 | Hubbard | 128/89 R |

*Primary Examiner*—Robert Bahr
*Assistant Examiner*—Philip Kubel
*Attorney, Agent, or Firm*—Fleit, Jacobson, Cohn, Price, Holman & Stern

[57] ABSTRACT

An arm board for supporting the forearm, wrist and hand during intravenous therapy includes a contoured support having adjoined forearm, wrist and hand support surfaces for conformally supporting the ventral surfaces of the forearm, wrist and palm. A handgrip is provided adjoining the palm support surface, and thumb recesses are provided on each side of the hand support to enable the patient to grip the support. A tubing support member is pivotally mounted at the handgrip to provide support for intravenous tubing. The tubing support member is mounted to be pivotable about its handgrip mounting as well as to be vertically adjustable with respect to the handgrip. The pivot mounting is contained within the handgrip and includes a locking or clamping mechanism which is manually operable via a thumbwheel accessible through the handgrip for fixing the tubing support in place.

9 Claims, 1 Drawing Sheet

U.S. Patent
June 25, 1991
5,025,801
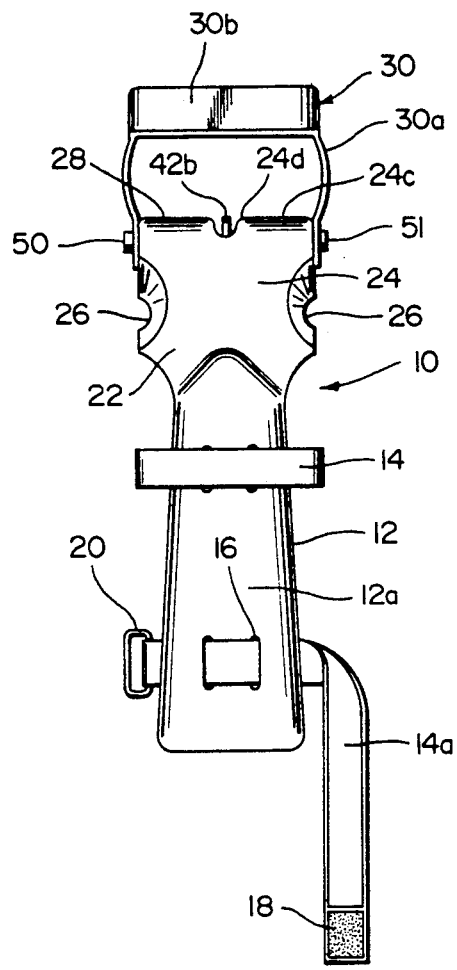
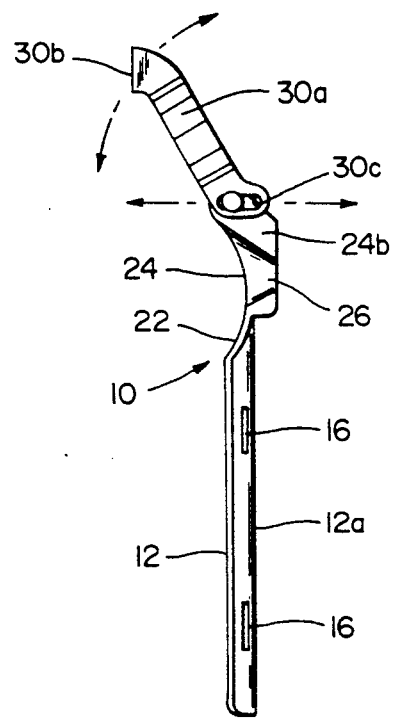
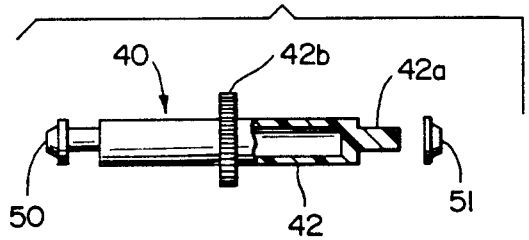
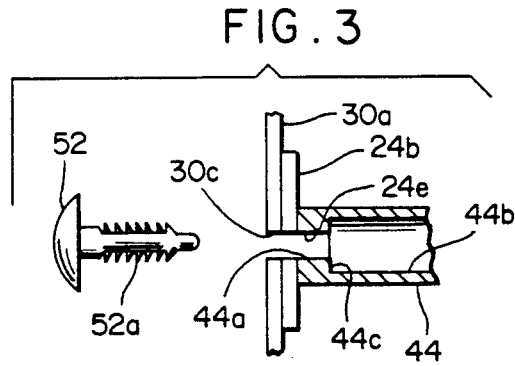
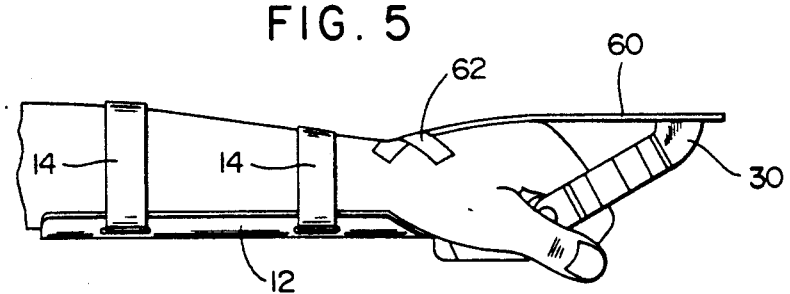

UNIVERSAL INTRAVENOUS ARM SUPPORT

BACKGROUND AND SUMMARY OF THE INVENTION

The present invention relates generally to an arm rest or support for supporting a patient's arm during intravenous therapy.

More particularly, the invention is directed to an arm rest or support which can comfortably support and immobilize a patient's arm during intravenous therapy while allowing finger movement of the patient's hand, thereby lessening patient tension.

In intravenous therapy, a needle attached to a tube is typically placed in a vein of the patient, typically proximate a limb joint such as at the elbow where the veins are closer to the skin and more accessible, and infusion, transfusion, phlebotomy or other procedures or therapies are performed by drawing or passing fluids through the tube. It is desirable in many instances to support the limb proximal its joint at the IV site, and in the past this has been accomplished typically by simply placing a short board or splint along the limb, and then securing the limb to the splint board as with tape, and the intravenous tubing might either be simply taped down along a portion of the patient's arm or typically be taped down or otherwise made fast to the splint as well, in order to prevent any movement of the IV needle in the vein or possible dislodgement of the IV needle from the vein. However, this practice often resulted in discomfort to the patient due to the nonconformability and stiffness of the splint board in contact with the limb and joint, and was intrusive upon the patient. Thus, it has been desirable to provide a means for more effectively supporting the patient's limb proximal the intravenous therapy site in a comfortable and non-intrusive manner, and for securing the tubing against dislodgement of the needle from the vein.

Moreover, there has been a need for an effective and comfortable yet simple and inexpensive forearm-to-hand IV support board means for IV therapy use which is adaptable for use on either arm and which includes a handgrip for enhancing patient comfort and security, and which also incorporates an IV tubing support means which can be adjusted positionally relative the forearm/wrist/hand in order to accommodate different situations. And in regard to the trend toward disposability for hygienic considerations, the simplification of medical treatment devices with attendant lowering of their cost to justify such disposability is highly desirable for economic reasons.

Various types of prior arm supports, immobilizers and restraints have been previously proposed for use in association with intravenous therapy. Typical of these prior devices is one disclosed in U.S. Pat. No. 2,693,794 and U.S. Pat. No. Des. 170,885 to Neville. This prior medical restraint includes a molded plastic main support member which is basically in the form of a half-cylinder and of a length extending along the arm from the patient's hand to a point well above the patient's elbow and approaching the shoulder. A forward end of this main support member is provided with a cutout, and across this forward end cutout extends a transverse gripping handle of cylindrical form secured to the forward ends of the main support member by clamping means. Neville describes that this cylindrical gripping handle should be at least about one inch or greater in diameter so as to enable the patient to feel and reflexively grip the handle securely, which gripping action by the patient on the handle is beneficial for both giving the patient a sense of security as well as for producing a clenching action which squeezes the blood out of the veins in the center of the patient's forearm thus forcing the blood to the veins under the skin for better visualization of the veins during intravenous therapy. The patient's arm is held in the restraint by flexible straps, and the restraint is provided with fastening points for a rubber tubing tourniquet which is passed through the bottom of the support member. Cutouts are provided in the sides of the restraint to permit access to veins along the sides of the elbow, while the upper side edges of the wrist portion and rear end of the support member extend high along the arm, and the side wall upper edges slant downwardly from the wrist to the forward end where the grip handle is secured. However, this device does not provide any means for securing the IV tubing thereto at a desired location with respect to the forearm, wrist and hand, nor is any means provided between the forward end of the support member and the handgrip for supporting the patient's wrist.

Another prior arm restraint device is known from U.S. Pat. No. 3,724,456 to Waxman which discloses an arm support attachment for intravenous therapy having a rigid member contoured for holding the extremity of a patient in a comfortable and anatomically correct position when laid upon a horizontal surface. The rigid member is formed of contoured upper and lower shell parts which at one end are arched and terminate in a contoured recess, for receiving the forearm, wrist and hand of a patient. Finger recesses are provided at this closed end along with thumb recesses along both sides. The patient's arm and wrist can be strapped to the rigid member. The shells are joined together at their edges, and can be positioned for supporting the patient's forearm and hand. The shells are fastened together to form a rigid member. A specially configured sterile liner is first placed on the contoured rigid member to be under the patient's arm, and then the IV needle is inserted into the patient's hand vein and the patient's hand, wrist and forearm are placed on the liner positioned on the contoured surface of the rigid member. A flap of the liner is then wrapped around the patient's hand to cover the IV and secured, and then straps are used to secure the patient's wrapped arm and hand to the rigid member. Because the rigid member shells have thumb recesses along both sides at their end next to the finger recesses, the restraint is "ambidextrous", i.e. it can accommodate the thumb of either hand and thus can support a patient's right or left arm. However, such a device, consisting of separate components assembled together and a separate liner element, is complex and, apart from the sterile liner element itself, is not intended for disposal after use.

U.S. Pat. No. 3,722,508 to Roberts discloses another prior device for immobilizing a limb joint during intravenous therapy. One disclosed embodiment includes an open-ended U-shaped channel across the upstanding edges of which is clamped a rigid arched infusion guard and having an extension at each end, the channel and its extensions being shaped complementary to the shape of the arm adjacent the elbow joint. In this device, the arm is fastened to the extensions with straps. In a modification, the forearm support channel is provided with an extension raised slightly relative the forearm support channel to complement the configuration of a slightly flexed wrist. Further forward of this wrist extension, a handgrip portion is provided about which the patient's fingers may pass, and a lateral opening is provided on one side of the handgrip portion for accommodating the patient's thumb. However, it is contemplated that four or five different sizes of such a device would be required in order to accommodate various patients on which this device might be employed. Also, no means are provided in this device for securing the IV tube in a desired location.

Still another prior device of this type is disclosed from U.S. Pat. No. 3,812,851 to Rodriguez which describes a slightly flexible arm support allowing limited elbow movement, and having a panel overlying the forearm and a support panel underlying the upper arm, these panels being joined by a flexible spiral section allowing limited flexure between the two panels. The overlying forearm panel is provided with upstanding posts for securing and holding IV tubing, the forearm and upper arm panels having straps for securing the patient's arm thereto. However, the position of the upper forearm support panel in this device is relatively fixed and thus not adjustable, nor are any means provided for supporting the patient's wrist or for gripping.

Another prior device is disclosed from U.S. Pat. No. 2,744,526 to Saylors which describes an arm restraint having a wire frame. In this device, a single rod is bent to form a frame having a U-shape at one end with an arched transverse portion. The rod parallel side portions of the frame extend along the arm, and at the forward end one of the rod ends is bent laterally to provide a core for a hand grip or end pad. The forward end of the other side frame rod is also bent forwardly of the handgrip to provide a strain relief rod to which IV tubing may be secured with clips. A pair of binding belts extend transversely between the side rods intermediate the frame ends to enable the restraint to be secured to the patient's forearm. However, this device does not support the ventral or lower surface of the patient's forearm and wrist, nor is the strain relief rod's position adjustable.

In U.S. Pat. No. 4,502,477 to Lewis there is disclosed a molded rigid splint formed to mate with a patient's forearm, wrist and hand, for use with an IV line and contemplated to be disposable or reusable. Side edges of the splint are rolled to provide grip channels along the sides of the splint in which channels IV tubes can be anchored, and the device further includes straps for binding the forearm and hand. However, in this device the IV tubing support means are fixed in position along the sides of the splint and thus cannot be adjustably positioned for different situations, and also necessarily require the IV tube to be run along the side of the splint.

The present invention is directed to overcoming the disadvantages and shortcomings of the prior devices, and provides an arm support of the so-called "arm board" or "splint" type which is generally conformally shaped or contoured to fit along the ventral surface or underside of a patient's forearm and wrist and which includes forearm, wrist and palm support portions and a handgrip for enhancing patient comfort and security. Recesses on both sides of the palm support portion adjacent the handgrip accommodate the thumb of either arm, permitting use of the invention on either the right or left arm of the patient. A pivotable tubing support is swingable about a pivot at the handgrip to adjustably position a support portion thereof above the patient's fingers and at the level of the posterior surface of the patient's hand and forearm for securing intravenous tubing at a location just adjacent the forearm and at the approximate level thereof. Advantageously, at its pivot the IV tubing support is adjustable vertically relative the arm and wrist support to accommodate various situations, and includes means for fixing the support securely in position. The adjustability of the position of the IV tubing support relative the forearm advantageously enables the IV tubing to be secured at a point approximately level with the forearm-wrist posterior surface and aligned with the needle insertion site, so that the IV tube can be run straight from the IV tubing support to the needle without any substantial bending of the IV tubing, thus avoiding undesirable flexure forces arising in the IV tubing length between its securing point at the support and the needle, which forces might deleteriously act upon the needle. The invention is of simple construction for low cost to enable its use as a "single use" disposable item if desired.

BRIEF DESCRIPTION OF THE DRAWINGS

The features and advantages of the universal intravenous arm support of the present invention will be made more apparent from the following detailed description taken together with the drawings, in which:

FIG. 1 is a top plan view of the universal intravenous arm support of the present invention;

FIG. 2 is a side view of the universal intravenous arm support of the present invention;

FIG. 3 is a partial sectional view of the adjustable tubing support pivot;

FIG. 4 is a view of a locking mechanism of the adjustable tubing support pivot; and FIG. 5 is a side view showing the universal intravenous arm support of the present invention in use.

DETAILED DESCRIPTION OF THE INVENTION

Referring to FIGS. 1 and 2, there is shown indicated generally at 10 the universal intravenous arm support of the present invention. Support 10 includes a longitudinal forearm support portion 12 which is curvedly shaped to conform generally with the contour of the ventral surface of a person's forearm above the wrist, having lateral edges which taper or converge inwardly towards the wrist while at the same time extending curvingly upwardly from the central bottom portion 12a to support the lower lateral margins of the forearm.

As may be seen from FIG. 5, a pair of straps 14 are used to secure patient's forearm to the support 10, and, as shown in FIGS. 1 and 2, in order to accommodate the straps 14, the forearm support portion 12 is pierced by two pairs of aligned slots 16 at spaced locations therealong, the slots 16 being spaced apart on respective sides of the central bottom portion 12a. Each of the straps 14 may thus be passed through one pair of slots 16, and each strap 14 is provided along an outer surface thereof with a Velcro strip 14a. Each strap 14 is also provided on one end thereof and on its outer surface with a Velcro closure member 18 which can interlock with the strip 14a. Each strap 14 is provided at its opposite end with a ring 20 through which the other end of the strap may be looped in order that the straps 14 can be folded back onto themselves to confront the strap outer surface of the folds. In this way, the folded-over strap portion can be fastened to the underlying strap portion by engaging the closure 18 with the strip 14a.

Proximal its convergent forward end, the forearm support portion 12 flattens in transition from a curved configuration to a generally planar or only slightly curved configuration, to provide a wrist support portion 22 which widens laterally, that is, the lateral edges of wrist support portion 22 widen outwardly from the forward end of forearm support 12, for supporting the underside of the patient's wrist.

Adjacent the wrist support portion 22 there inclines slightly curvedly upwardly a wide hand or palm support portion 24 the side edges 24a of which are straight and extend downwardly below the level of the bottom of the forearm support portion 12 to provide a flat base 24b which elevates the palm support portion 24 by virtue of which the forearm support portion 12 will be caused to be inclined slightly upwardly when the support 10 is placed upon a surface. At each of its sides, the palm support portion 24 is provided with contoured thumb recesses 26 for receiving the thumb of either hand.

The forward end margin 24c of palm support portion 24 is rolled-over to provide a semi-cylindrical handgrip portion 28 around which the patient's fingers may curl for gripping. At the handgrip portion 28 there is provided centrally a notch 24d formed in the forward end margin 24c for access to the locking mechanism of the tubing support means described below.

Referring now to FIGS. 1 through 5, the support 10 also includes a pivotable IV tubing support member 30. Tubing support member 30 has a pair of lateral arms 30a which are pivotally and adjustably mounted at their free ends to the handgrip portion 28 by means of a an adjustable and lockable pivot mechanism 40. A tubing support platform 30b transversely bridges the pair of lateral arms 30a and provides a flat wide surface on which intravenous tubing may be supported and secured. The free ends of lateral arms 30a are provided with vertical slots 30c therethrough for receiving the pivot mechanism. These free ends of the lateral arms 30a are placed over and slide on the side edges 24b at the handgrip portion 28, with the slots 30c being aligned with through holes 24e in the side edges 24b at the handgrip portion 28. The lateral arms 30a may be bowed slightly outwardly in their medial portion between their free ends and the tubing support platform 30b in order to provide adequate lateral clearance for the patient's hand.

The lockable pivot mechanism 40 includes a cylindrical pivot body 42 which at one end is provided with a pivot pin 42a. A thumbwheel 42b is provided at the medial portion of the pivot body 42. The pivot body 42 is internally threaded or is provided internally with a threaded insert to accept, at its end opposite the pivot pin 42a, the threads of a screw 50. A cap 51 is fastenable on the end of the pivot pin 42a.

The pivot body 42 is installed within the handgrip so that the pivot pin 42a projects outwardly through one of the through holes 24e in the side edge 24b, and through the slot 30c of one lateral arm 30a of the tubing support 30. The cap 51 is fastened to the end of the pivot pin 42a so as to pivotally fix the one side of the tubing support 30 to the handgrip. The threaded shaft of screw 50 is then passed through the other arm slot 30c and through hole 24e, and is threadedly engaged in the internal thread at the other end of the pivot body 40. The threading of the screw 50 in the pivot body 42 is easily accomplished by manually turning the thumbwheel 42b to rotate the pivot body, the notch 24d allowing access to the thumbwheel 42b.

It will be appreciated that the pivot pin 42a and the shaft of the screw 50 serve as pivots for permitting the swinging rotation movement of the tubing support 30 thereabout, which movement is indicated by the dash-dot arrows in FIG. 2. It will also be appreciated that by virtue of the elongated vertical slots in the pivot ends of the arms 30a, the tubing support 30 may also be raised and lowered on these pivot points, for effectively moving the tubing support platform 30b farther away from or closer to the forward end of the support member 10, this motion being depicted by the dashed arrows in FIG. 2. It will further be appreciated that because of the forward inclination of the arms 30a (e.g. 45°), the tubing support platform 30b lies generally on the horizontal, and, because of the vertical elongation of the slots 30c, the platform 30b will remain parallel to the horizontal upon vertical movement of the tubing support 30. In operation, the tubing support 30 may be pivoted around the pivot points 42a, 50 to place the platform 30b generally parallel with the posterior surface of the patient's hand at the needle insertion site, and the tubing support raised or lowered via slots 30c on the pivot points 42a, 50 to place the tubing support platform 30b approximately level with the posterior surface of the patient's hand at the needle insertion site, so that the IV tube 60 can be supported by its passage over the platform 30 at the approximate level of the needle insertion site 62 as shown in FIG. 5. The tube 60 may then be secured to the platform 30b as with tape or by other suitable means in order to immobilize the tubing proximate the needle insertion site 62. The adjustability of the tubing support 30 relative the support 10 thus allows flexing of the tubing 60 to be minimized between the tubing support 30 and the needle insertion site 62 to reduce risk of any forces arising in the tubing which might cause undesirable movement of the needle, thus reducing risk of trauma at the needle insertion site and enhancing patient comfort.

Once the tubing support 30 has been properly positioned, it may be locked in place against moving relative the support 10 by manipulating the thumbwheel 42b so as to rotate pivot body 42 to tighten the screw 50 thereinto until the arm 30a of the tubing support 30 and the side edge 24b of the handgrip portion 28 are clamped tightly together between the end of pivot body 42 and the head of the screw 50, thus securing the tubing support 30 in place.

It may be preferable to replace the pivot pin 42a with a threaded pivot, that is, by internally threading both ends of the pivot body but with oppositely directed threads at the respective ends in the fashion of a turnbuckle, and into each end insert a correspondingly oppositely threaded screw 50, so that rotation of the thumbwheel would tighten or loosen both screws simultaneously to obtain clamping or loosening of the both pivots Additionally, it may be preferred to utilize locking washers between the screw head and arm 30b and/or between the arm 30b and side edge 24c to enhance the clamping force therebetween when the screw 50 is tightened.

In FIG. 3 there is shown a modification of the pivot mechanism 40 in which the pivot pin 42a has been replaced by a separate headed pin fastener or retainer 52. The pivot body 44 is provided with an end bore 44a into which may be engagingly inserted the barbed shaft 52a of the fastener 52. The end bore 44a opens into a larger central bore 44b, with a shoulder 44c being formed thereby for retaining engagement by the barbed shaft 52 of fastener 52.

As shown in FIG. 5, the patient's forearm is strapped to the support 10 by means of the straps 14, the forearm, wrist and hand are continuously supported along their ventral surfaces by the forearm support 12, wrist support 22 and palm support 24, and the patient's thumb and fingers are enabled to comfortably grip the support 10 by means of the thumb recesses 26 and handgrip 28. Furthermore, by virtue of the contouring of the respective forearm, wrist and palm support portions of the support 10, the patient's arm, wrist and hand may be optimally supported in an orientation which presents little discomfort to the patient yet facilitates palpation and visualization of a desired vein and the insertion and retention of the IV needle therein. And because of the provision of the adjustably positionable tubing support 30, the IV tube can secured against movement in an optimum orientation without causing patient discomfort and with reduced risk of needle movement.

Having now described the invention, it will be appreciated that it is amenable to various modifications without departing from the scope of the invention, which is intended to be limited only by the appended claims.

What is claimed:

1. An arm support for intravenous therapy, comprising:

forearm support means contoured to conform with the ventral surface of a patient's forearm, for supporting the patient's forearm thereon;

means for securing the forearm of the patient to said forearm support means;

wrist support means adjoining said forearm support means and contoured to conform with the ventral surface of the patient's wrist, for supporting the patient's wrist thereon;

hand support means adjoining said wrist support means and contoured to conform generally to the palm and thumb of the patient, for supporting the palm and thumb of the patient thereon;

handgrip means adjoining said hand support means and contoured for accommodating gripping by the fingers of the patient's hand;

tubing support means pivotally mounted to said handgrip means for pivotal movement relative thereto, for providing a support surface for intravenous tubing adjacent and approximately level with the posterior of the patient's hand, wrist and forearm; and locking means for locking said tubing support means to said handgrip for preventing movement therebetween.

2. An arm support for intravenous therapy according to claim 1, wherein the tubing support means includes a pair of lateral arms each joined at one end thereof to a support platform, free ends of said lateral arms being formed with aligned elongate slots therethrough.

3. An arm support for intravenous therapy according to claim 1, wherein the locking means includes a cylindrical pivot body mounted within said handgrip means, to the ends of which pivot body are pivotally mounted the tubing support means, and clamping means for producing clamping force between said tubing support means and said pivot body.

4. An arm support for intravenous therapy according to claim 3, wherein said pivot body is provided with manually operable thumbwheel means for operating said clamping means.

5. An arm support for intravenous therapy according to claim 3, wherein said handgrip means is formed with an aperture therein for access to said thumbwheel means of said pivot body.

6. An arm support for intravenous therapy according to claim 2, wherein said support platform is flat, and wherein said lateral arms are inclined at approximately 45° to the plane of said support platform.

7. An arm support for intravenous therapy according to claim 3, wherein said pivot body is provided at its one end with a projecting pivot pin and at its other end is internally threaded, and wherein said clamping means is a screw threadedly engaging the internal thread of the pivot body.

8. An arm support for intravenous therapy according to claim 3, wherein said pivot body is internally threaded at each end thereof, and wherein said clamping means is a screw threadedly engaging each internal thread of the pivot body.

9. An arm support for intravenous therapy according to claim 3, wherein said pivot body is internally threaded at one end thereof and at its other end is provided with a bore for receiving a retainer therein, and wherein said clamping means is a screw threadedly engaging the internal thread of the pivot body.

* * * * *